(12) United States Patent
Ford (10) Patent No.: US 8,323,565 B2
(45) Date of Patent: Dec. 4, 2012

(54) CRUCIBLE SHUTTLE ASSEMBLY AND METHOD OF OPERATION

(75) Inventor: Gordon C. Ford, St. Joseph, MI (US)

(73) Assignee: Leco Corporation, St. Joseph, MI (US)

( * ) Notice: Subject to any disclaimer, the term of this patent is extended or adjusted under 35 U.S.C. 154(b) by 1288 days.

(21) Appl. No.: 12/055,880

(22) Filed: Mar. 26, 2008

(65) Prior Publication Data

US 2008/0253870 A1 Oct. 16, 2008

Related U.S. Application Data

(60) Provisional application No. 60/911,320, filed on Apr. 12, 2007.

(51) Int. Cl.
*G01N 21/00* (2006.01)
(52) U.S. Cl. .......................................... 422/63; 414/586
(58) Field of Classification Search ........................ None
See application file for complete search history.

(56) References Cited

U.S. PATENT DOCUMENTS

| | | | |
|---|---|---|---|
| 4,238,450 A * | 12/1980 | Bredeweg et al. | 422/63 |
| 4,456,580 A | 6/1984 | Yamada et al. | |
| 4,573,910 A | 3/1986 | Bredeweg | |
| 5,395,586 A | 3/1995 | Hemzy et al. | |
| 5,441,891 A | 8/1995 | Burkovich et al. | |
| 5,585,068 A | 12/1996 | Panetz et al. | |
| 6,117,391 A | 9/2000 | Mootz et al. | |
| 6,551,833 B1 | 4/2003 | Lehtinen et al. | |
| 7,402,280 B2 | 7/2008 | Ford | |
| 7,695,239 B2 * | 4/2010 | Wu | 414/783 |
| 2003/0175156 A1 | 9/2003 | Ford | |

* cited by examiner

*Primary Examiner* — Saul Rodriguez
*Assistant Examiner* — Willie Berry, Jr.
(74) *Attorney, Agent, or Firm* — Price Heneveld LLP (57) ABSTRACT

A crucible handling shuttle includes a pair of opposed dual crucible-gripping arms mounted on a rotatable head and moves between an induction furnace pedestal and a crucible loading station, such that one pair of arms pick up a crucible loaded with a preweighed sample, the shuttle moves to the induction furnace, where the other pair of arms grip and remove a spent crucible. The shutter head then rotates to deposit the new sample-holding crucible onto the pedestal and subsequently moves out of the furnace area to a sample disposal chute positioned between the crucible loading station and the furnace, whereupon the spent crucible is dropped for disposal. The shuttle head is then rotated and moved to the loading station to pick up a new crucible.

11 Claims, 13 Drawing Sheets

CRUCIBLE SHUTTLE ASSEMBLY AND METHOD OF OPERATION

CROSS-REFERENCE TO RELATED APPLICATIONS

This application claims priority under 35 U.S.C. §119(e) on U.S. Provisional Application No. 60/911,320, entitled CRUCIBLE LOADING/UNLOADING ASSEMBLY WITH OPPOSED DUAL GRIPPERS, filed on Apr. 12, 2007, by Gordon C. Ford, the entire disclosure of which is incorporated herein by reference.

BACKGROUND OF THE INVENTION

The present invention relates to a crucible loading/unloading assembly for efficiently moving crucibles onto and from the pedestal of an analyzer furnace.

Analyzers are used in the steel industry inter alia for determining the content of carbon and/or sulfur. Such analyzers include, for example, Model No. CS600 which is commercially available from Leco Corporation of St. Joseph, Mich. In the past, several systems have been designed to provide automatic loading and unloading of crucibles into such furnaces to provide more efficient throughput of samples. One such system is represented in, for example, U.S. Pat. No. 4,238,450. Also, sample combustion boats have been the subject of auto-loading, as shown in U.S. Pat. No. 5,395,586. U.S. Patent Publication 2003/0175156 also discloses yet another crucible loading system.

Such automated systems represent a significant advance over manually handling of spent crucibles and the potential for injury. However such systems either utilize a sequential multi-step process in which a spent crucible is removed and disposed of and subsequently a new crucible is placed on the induction furnace pedestal for introduction into the furnace or do not handle spent crucibles which must be manually removed. Such systems, although preferable to the manual introduction and removal of crucibles, leave room for improvement to increase the throughput of multiple specimens for analysis.

There remains a need, therefore, for an improved crucible loading and unloading system, particularly without requiring operator intervention in handling spent crucibles and substantially simultaneously reloading a new sample-holding crucible onto a furnace pedestal.

SUMMARY OF THE INVENTION

The system of the present invention accomplishes this goal by providing a crucible handling shuttle having a pair of opposed dual crucible-gripping arms which are mounted on a rotatable platform and moves between a crucible loading station and the induction furnace pedestal. One pair of arms picks up a crucible loaded with a preweighed sample, and the shuttle moves to the induction furnace, where the other pair of arms grip and remove the spent crucible. The shuttle then rotates to deposit the new sample-holding crucible onto the pedestal and subsequently linearly moves out of the furnace area to a crucible disposal chute positioned between the crucible loading station and the furnace, into which the spent crucible is dropped for disposal. The shuttle is then rotated and moved to pick up a new crucible with the same one pair of arms. This method of operation uses the same pair of arms to handle clean crucibles and the other pair of arms to handle spent contaminated crucibles.

Such an assembly provides the capability of handling two crucibles simultaneously for removing a crucible from an induction furnace pedestal and placing a new sample-holding crucible onto the pedestal. It also disposes of the spent crucible and picks up a new crucible in rapid sequence and while an analysis is being run. The resultant system can be employed with a crucible loading station handling a plurality of preloaded crucibles which are sequentially positioned to be picked up by the gripper arms, thereby greatly improving the throughput of samples for analysis.

According to other aspects of the invention, a system is provided for moving articles between at least first and second positions and includes pairs of opposed gripping arms for simultaneously gripping two articles on opposite sides of an axis of rotation, a rotating head supporting said arms, and a linear drive coupled to said rotating platform for moving said gripping arms between a first position and a second position.

According to another aspect of the invention, a method of loading and unloading crucibles to and from a furnace associated with an analyzer includes the steps of picking up a crucible at a loading station with one pair of crucible arms on a shuttle including pairs of opposed crucible-gripping arms for simultaneously gripping crucibles on opposite sides of an axis of rotation, moving the shuttle to a crucible-holding pedestal of a furnace, rotating the pairs of arms, picking up a spent crucible from the pedestal with another pair of arms of the shuttle, and rotating the shuttle and depositing a new crucible on the crucible-holding pedestal of a furnace.

These and other features, objects and advantages of the present invention will become apparent upon reading the following description thereof together with reference to the accompanying drawings.

DETAILED DESCRIPTION OF THE PREFERRED EMBODIMENT

Figure 1:
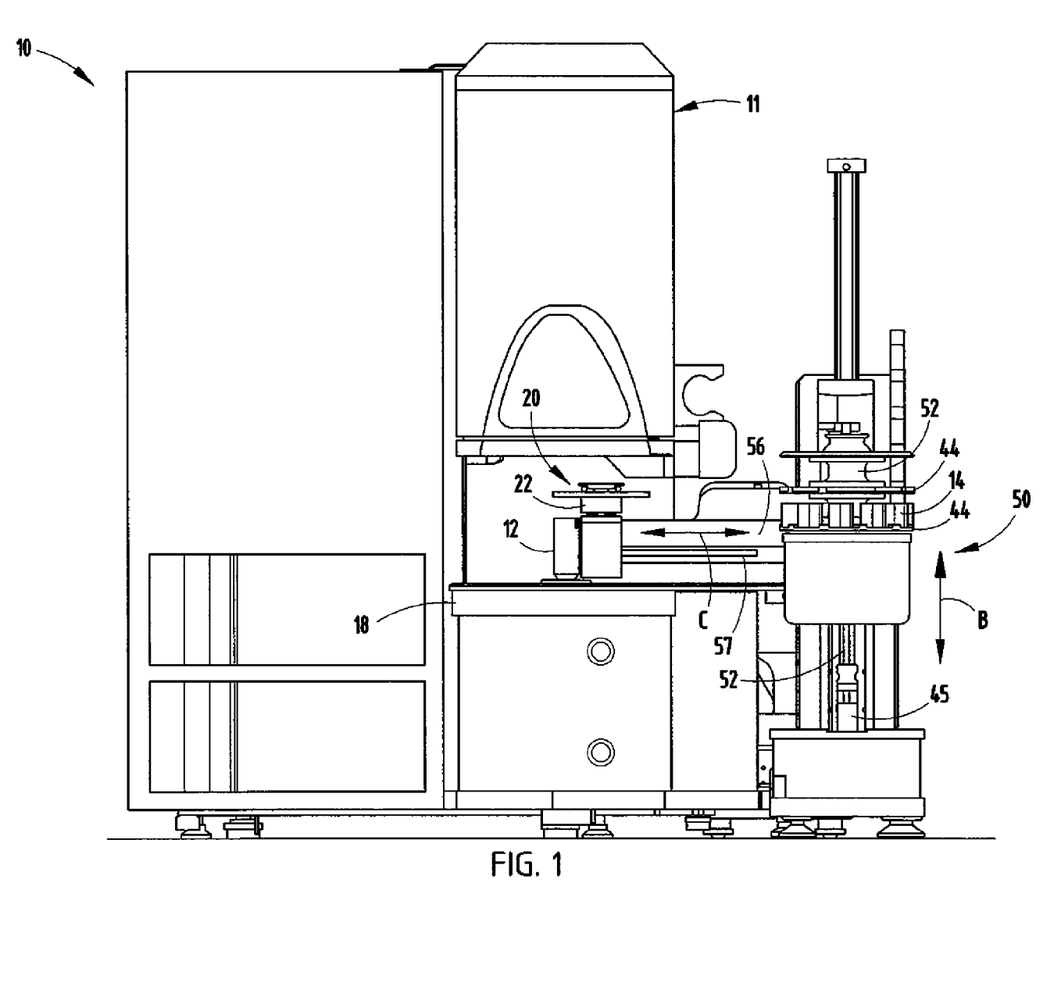
FIG. 1 is a front elevation view of an analyzer including an induction furnace including a crucible loading and unloading shuttle of the present invention together with a crucible loading station.

Referring initially to FIG. 1, there is shown an analyzer 10, such as a Model No. CS600, commercially available from Leco Corporation of St. Joseph, Mich. The analyzer includes an induction furnace 11 and the crucible loading/unloading shuttle assembly 20 of the present invention. Induction furnace 11 includes a crucible-holding pedestal 12, which moves vertically upwardly and downwardly as indicated by arrow A in FIG. 3, to introduce a sample-holding crucible 14 into the furnace for the combustion of and analysis of a specimen held therein. The pedestal is shown in its lowered position in FIGS. 1 and 3-5. A plurality of crucibles 14 each have preloaded and preweighed samples 13 (shown in phantom in FIG. 2) and are held in a vertical sample loading station 50, which may include up to six tiers of crucible-holding disks 44, each including ten crucible-holding sockets. The disks 44 are mounted in vertically spaced relationship on a vertically extending rotary axle 52 which can be raised and lowered, as shown by arrow B in FIGS. 1 and 2, to position a crucible, such as crucible 14' (FIG. 2) to a position to be picked up by gripper arms 26 of shuttle assembly 20. As crucibles 14 are picked from the loading station 50 the disk 44 aligned with the shuttle 16 of shuttle assembly 20 rotates to place the next crucible in position to be picked up. Once a disk 44 is fully unloaded, the shaft 52 is raised by a hydraulic, electric, or pneumatic cylinder 45 (FIG. 1) to position the next fully loaded disk 44 in position to dispense crucibles to shuttle 16.

Figure 7:
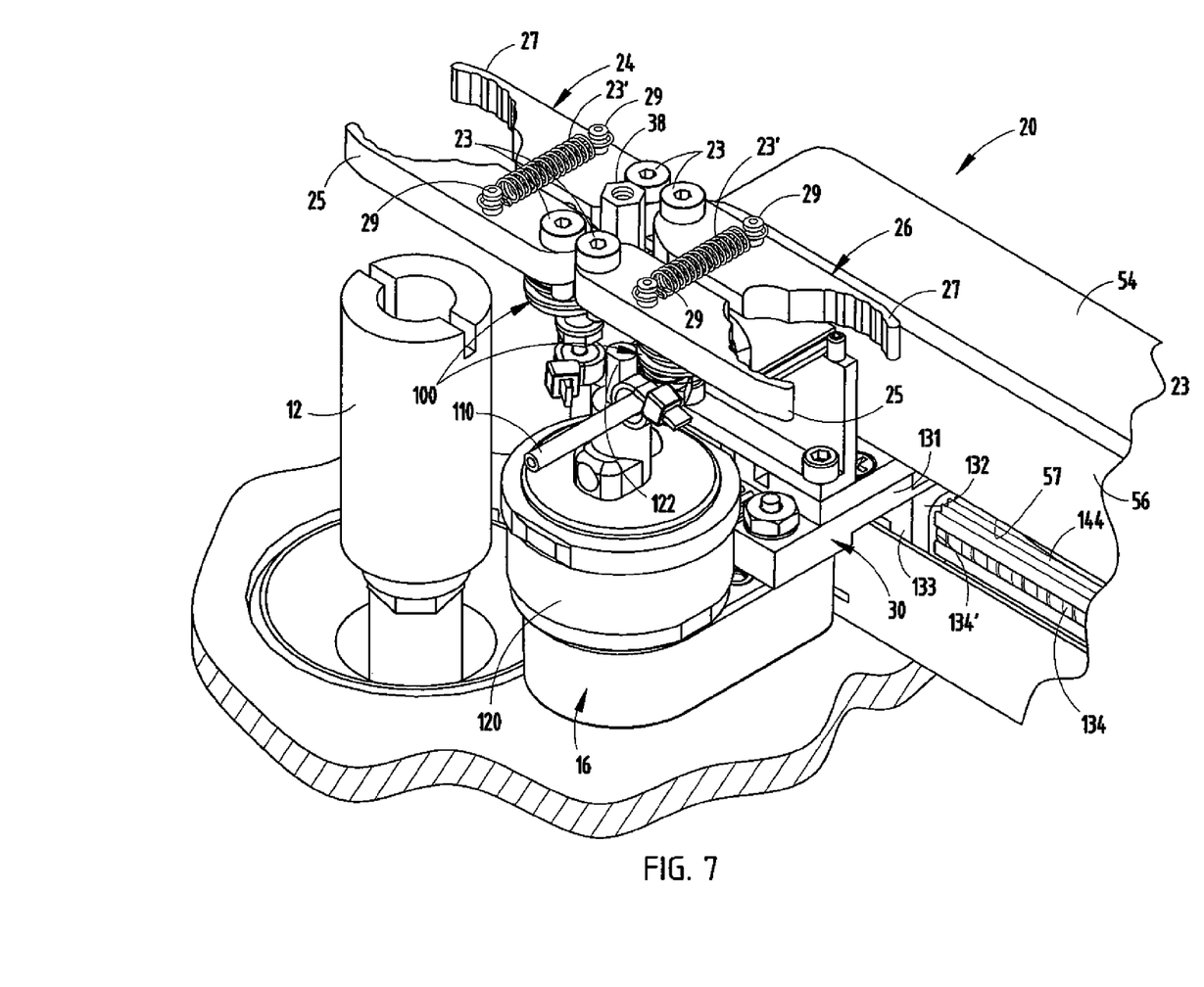
FIG. 7 is an enlarged fragmentary perspective partly broken-away view of the spring-loaded dual gripping arms of the shuttle of the present invention, shown without the housing.
Figure 8:
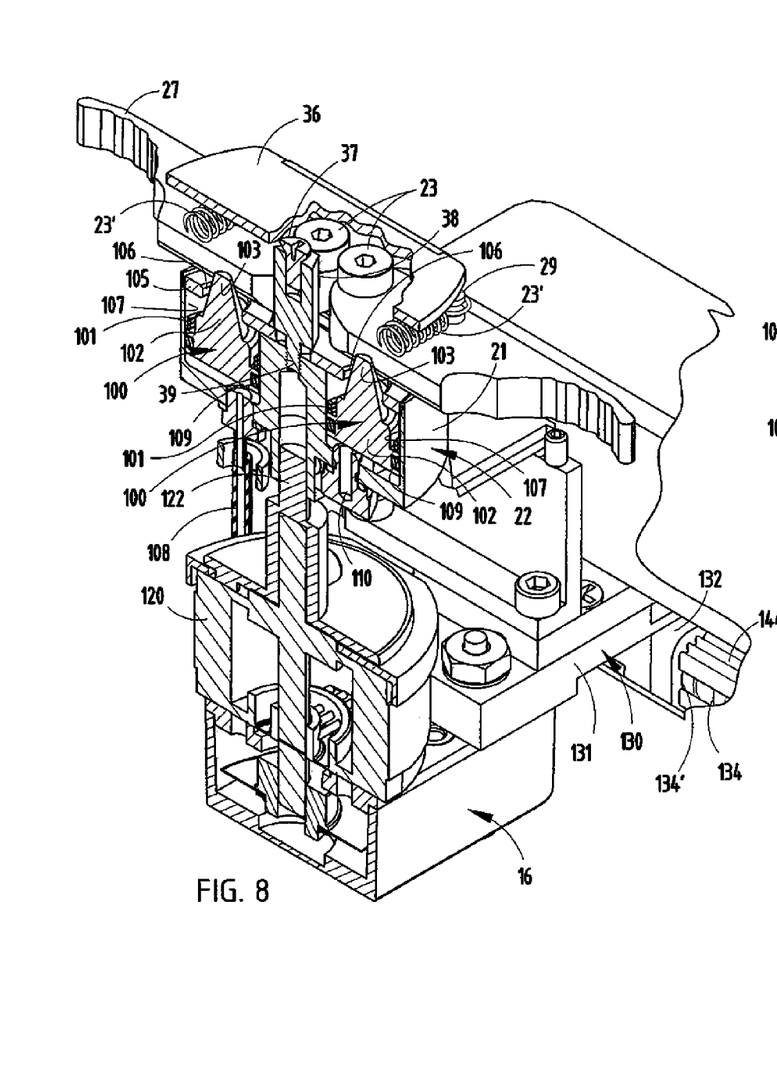
FIG. 8 is a partly broken away, vertical cross-sectional view of the structure shown in FIG. 7 taken along section line VIII-VIII of FIG. 3.

The shuttle assembly 20 includes, as best seen in FIGS. 2-5 and 7, a shuttle 16 with a rotary head 22 to which opposed pairs 24, 26 of spring-loaded, curved facing opposed gripping arms are mounted. Each pair of arms includes arms 25, 27 (best seen in FIG. 7), which are curved to circumscribe opposite sides of a cylindrical crucible 14 to hold crucibles in the shuttle 16 as it linearly moves between the sample loading station 50 in a direction indicated by arrow C in FIGS. 1 and 2 toward and away from furnace pedestal 12. Each of the arms 25, 27 are pivotally mounted to the top 121 of housing 21 (FIG. 8A) of rotary head 22 by pivot pins 23 (FIGS. 7 and 8). Springs 23' are coupled between each arm 25, 27 over posts 29 at a location spaced from their pivot connection to housing 21 of rotary head 22 to urge arms 25, 27 together for gripping the crucibles. The details of the operation of the gripping arms are described below.

Figure 2:
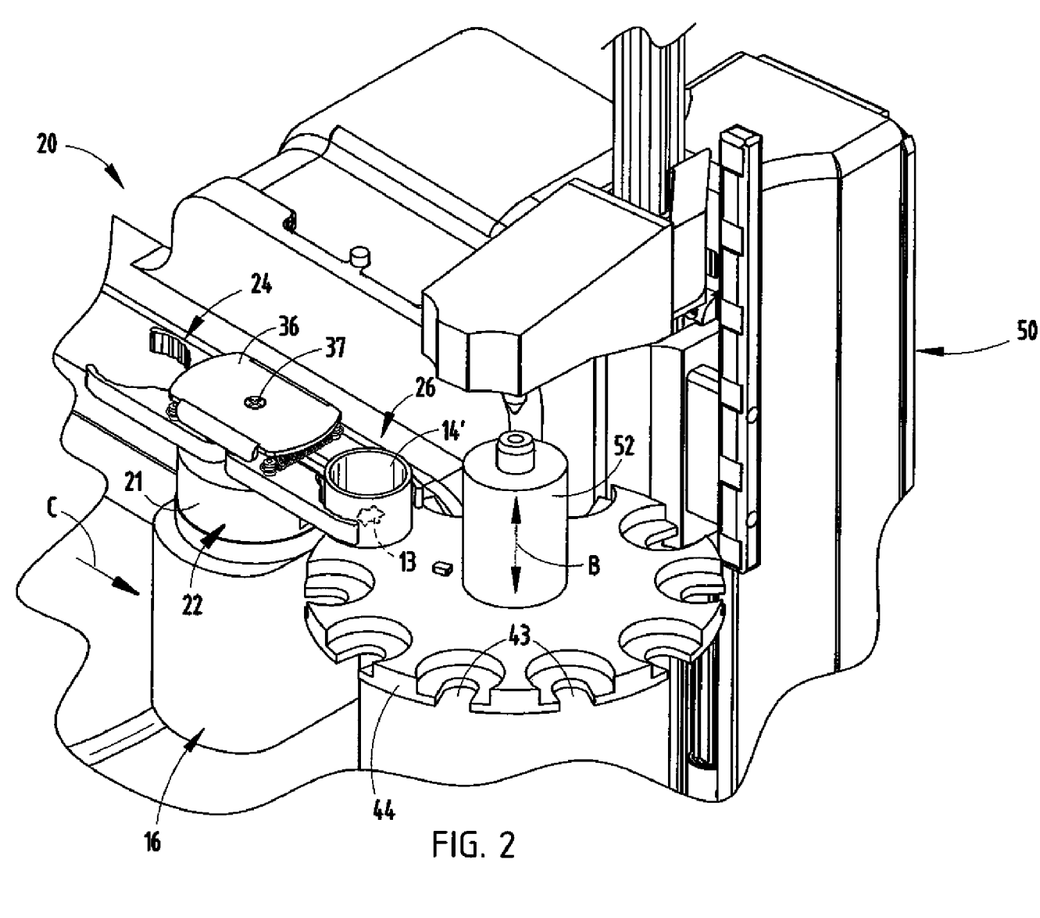
FIG. 2 is a fragmentary perspective view of the structure shown in FIG. 1, shown with the shuttle picking up a new sample-holding crucible from the crucible loading station.
Figure 3:
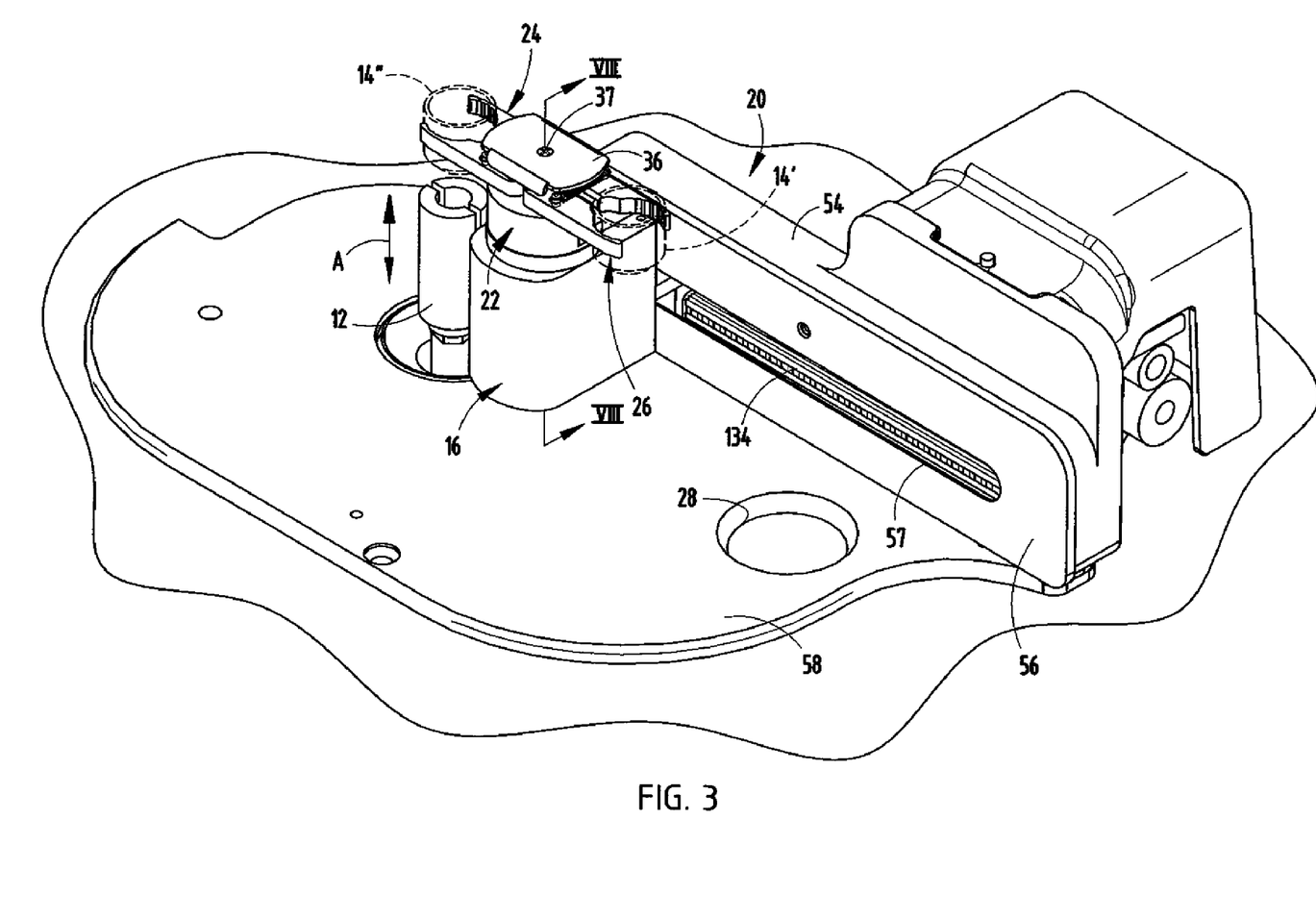
FIG. 3 is a fragmentary perspective view of the structure shown in FIG. 1, shown with the shuttle moved into position picking up a spent crucible from an induction furnace pedestal and about to rotate to place a new sample-holding crucible onto the furnace pedestal.

The shuttle 16 is mounted to a carriage 130 (FIGS. 7-10) for its linear movement between a new crucible picking position (FIG. 2) to the induction furnace pedestal 12, as shown in FIG. 3. Once at pedestal 12, the gripping arms 25, 27 are sequentially actuated to open and pick up the spent crucible 14" as shown in FIG. 3 whereupon the rotary head 22 rotates, as shown by arrow D in FIG. 4, to position the newly picked up crucible 14' onto the pedestal 12, as shown in FIG. 5. After depositing the new sample-holding crucible 14' onto pedestal 12, the shuttle 16 moves from the position shown in FIGS. 3-4 to the intermediate position shown in FIG. 5, whereupon the spent crucible 14" (FIG. 5) is dropped into a discharge chute 28 in base plate 58 by the opening of the gripping arms associated therewith. Subsequently, rotating head 22 of shuttle 16 is again rotated 180° and moved into the right endmost position shown in FIG. 2 to allow arms 26 to pick up the next sample-loaded crucible positioned by the rotation and/or raising of a crucible-holding disk 44 in the rotary crucible loading station 50 to present a new crucible to arms 26. Thus, only the pair of arms 26 engage clean crucibles while only the pair of arms 24 engage contaminated spent crucibles to assure the integrity of the analytical sequence. The method of handling the crucibles including the sequence of operation of the shuttle is now described in conjunction with FIG. 6.

Figure 6:
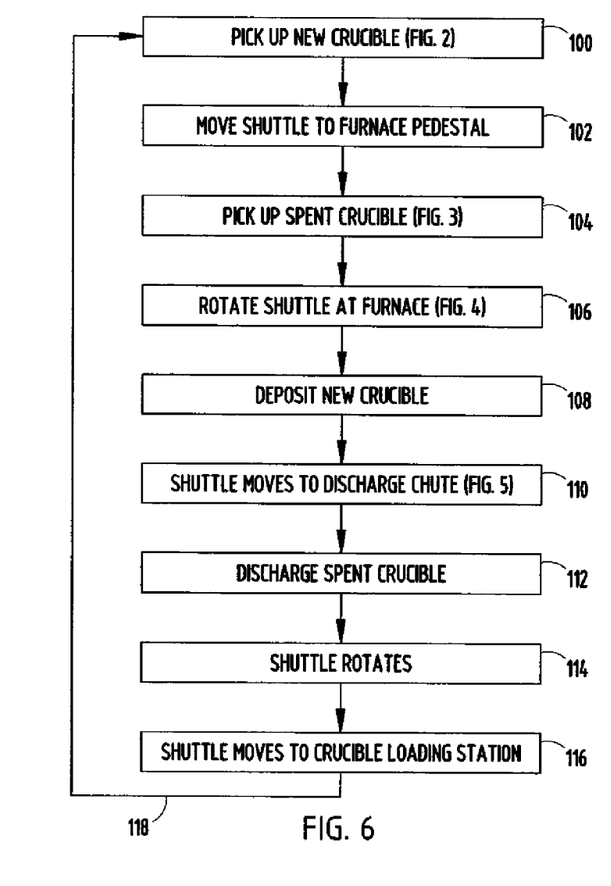
FIG. 6 is a block flow diagram of the method of handling the crucibles with the shuttle of the present invention.

As seen in FIG. 6 block 100, a sample loaded new crucible 14' such as shown in FIG. 2 is picked up by the pair of arms 26 which are opened as described below as the shuttle 16 moves to the loading station 50 to pick up a new sample-holding crucible 14'. The arms are then closed to grip the crucible, and disk 44 is lowered to eliminate any contact between crucible 14' and disk 44. Then, as the shuttle moves away from disk 44 toward the furnace pedestal, the crucible is removed from the slotted holding aperture 43 (FIG. 2) in the crucible-holding disk 44 of loading station 50. The shuttle then moves toward the pedestal 12 as seen by block 102 in FIG. 6 and as it approaches the pedestal with the arms 24 facing the pedestal, the arms are opened to circumscribe a spent crucible on the pedestal which has been lowered automatically from the furnace 11 after an analysis has been completed. The arms 24 then close around the spent crucible 14" and the carriage 130, and rotary head 22 is raised, as described below, to lift the spent crucible 14" off of the pedestal 12 as shown by block 104.

Figure 4:
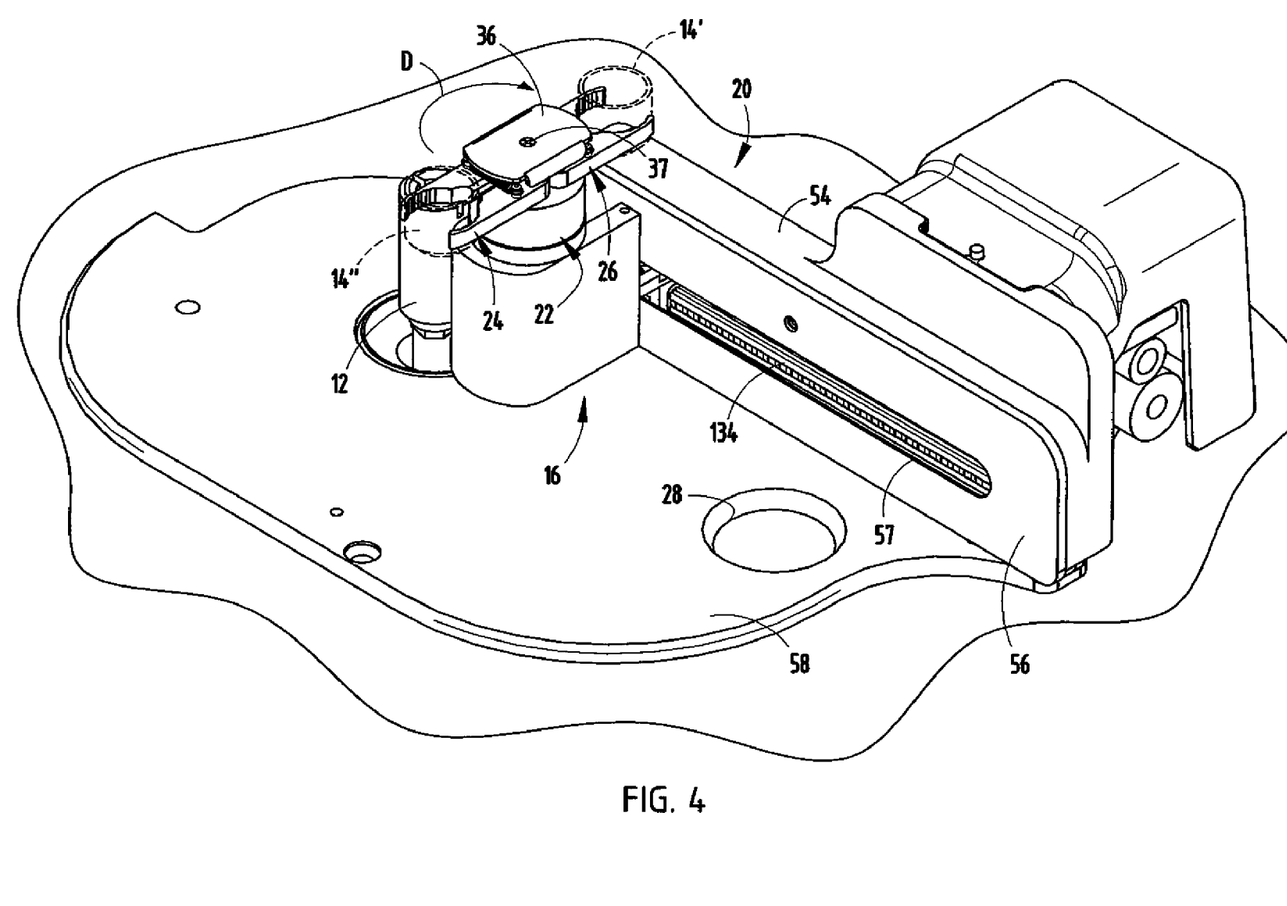
FIG. 4 is a perspective view of the structure shown in FIG. 3, showing the rotation of the shuttle toward a position to position a new crucible on the furnace pedestal.
Figure 5:
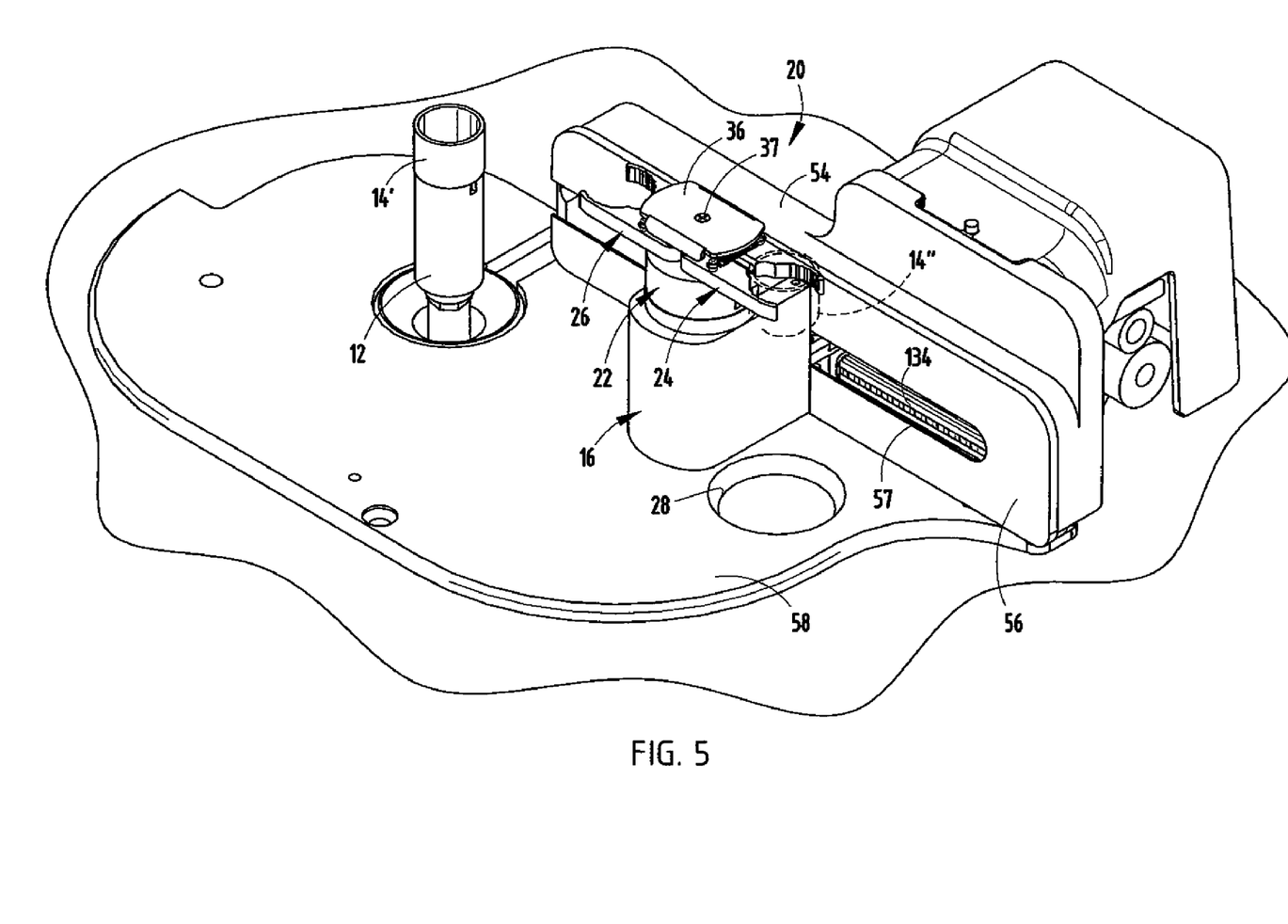
FIG. 5 is a perspective view of the structure shown in FIG. 3 with the new sample loaded crucible placed on the induction furnace pedestal and the spent crucible moved to a position for dropping it into a discharge chute.

The rotary head 22 of shuttle 16 is then rotated 180°, as illustrated in FIG. 4 and represented by block 106. Upon completion of the rotation of head 22, the new crucible 14' is aligned over the pedestal 12 and the rotary head and carriage is lowered to place the crucible 14' on the pedestal at which time arms 26 are opened to deposit the new crucible on the pedestal as shown by block 108. Once this has been done, as show by block 110 and FIG. 5, the shuttle moves to align the spent crucible 14" over the discharge chute 28 in base plate 58. The pair of arms 24 are then opened to drop crucible 14" down chute 28 for disposal as seen by block 112. The rotary head 22 of shuttle 16 is then rotated 180° again to position the pair of arms 26 in a position facing crucible loading station 50 as seen by block 114 and the arms are opened as the shuttle moves to the crucible loading station as shown by block 116 into the position shown in FIG. 2. As seen by line 118 in FIG. 6 the crucible handling sequence is then repeated until all of the crucibles holding samples to be analyzed have been sequentially introduced into the analyzer 10 and an analysis run on the samples. The sequence shown in FIG. 6 is programmed into the microprocessor 72 which is part of the control circuit 70 described below in conjunction with FIG. 13.

Figure 8A:
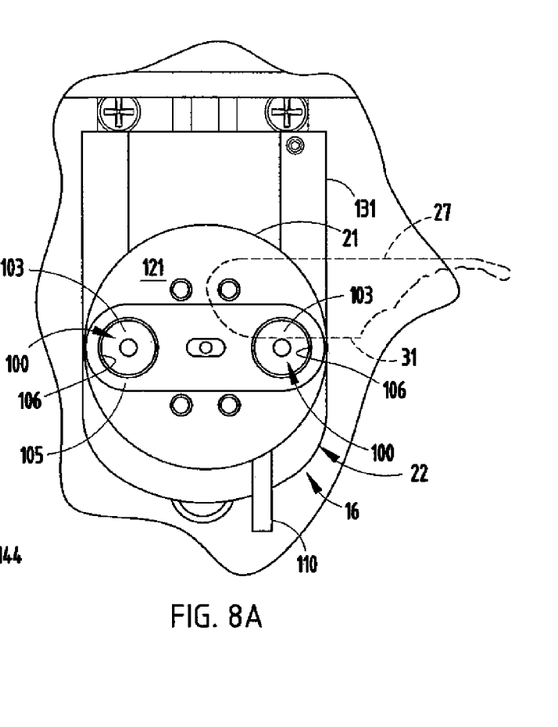
FIG. 8A is a top plan view of the gripping arm actuating pistons with one of the arms shown in phantom form.
Figures 9, 9A:
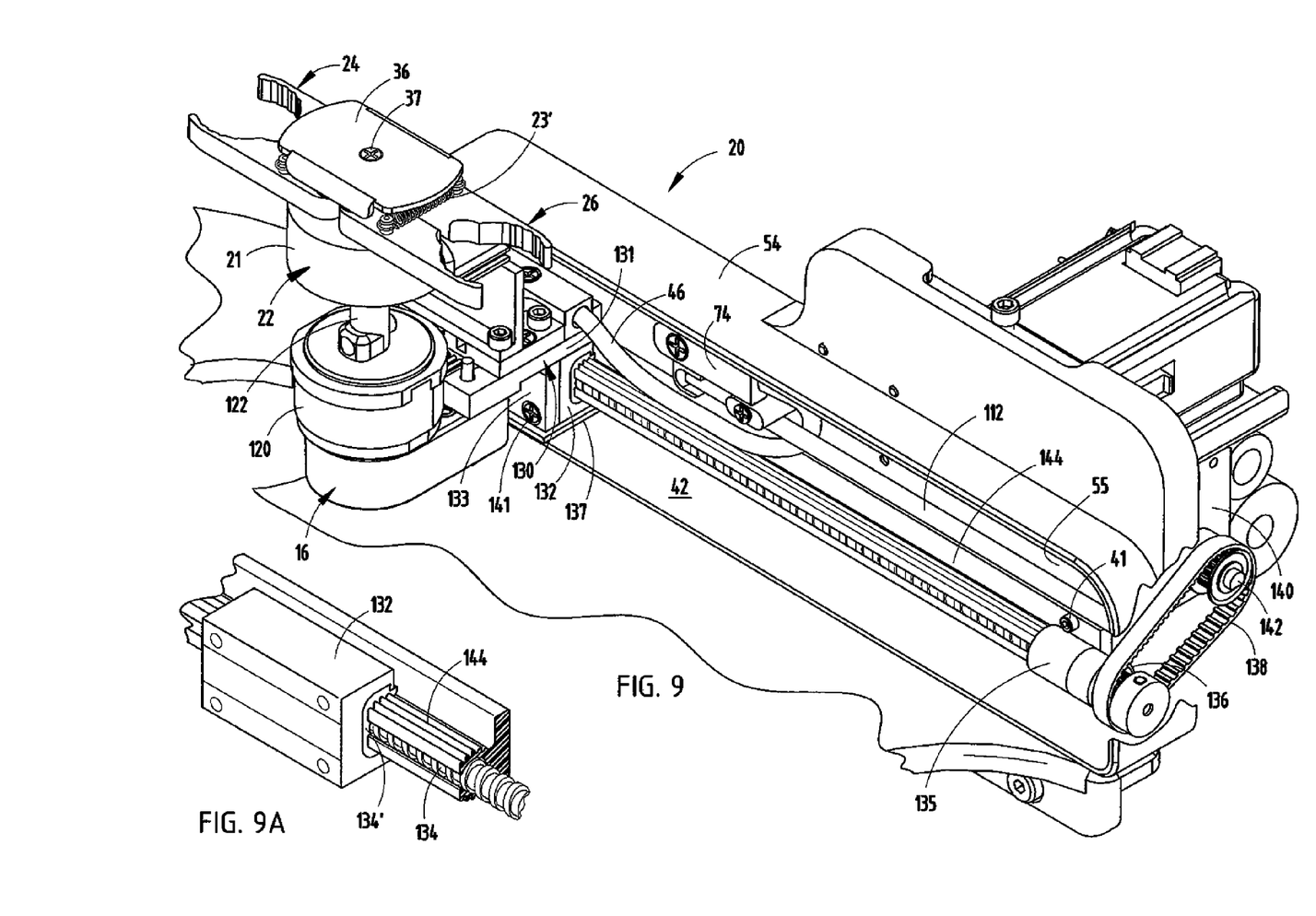
FIG. 9 is an enlarged fragmentary perspective view, partly broken away, of the linear drive of the shuttle assembly.
FIG. 9A is an enlarged fragmentary cross-sectional view of the drive screw and drive nut for the shuttle.
Figure 10:
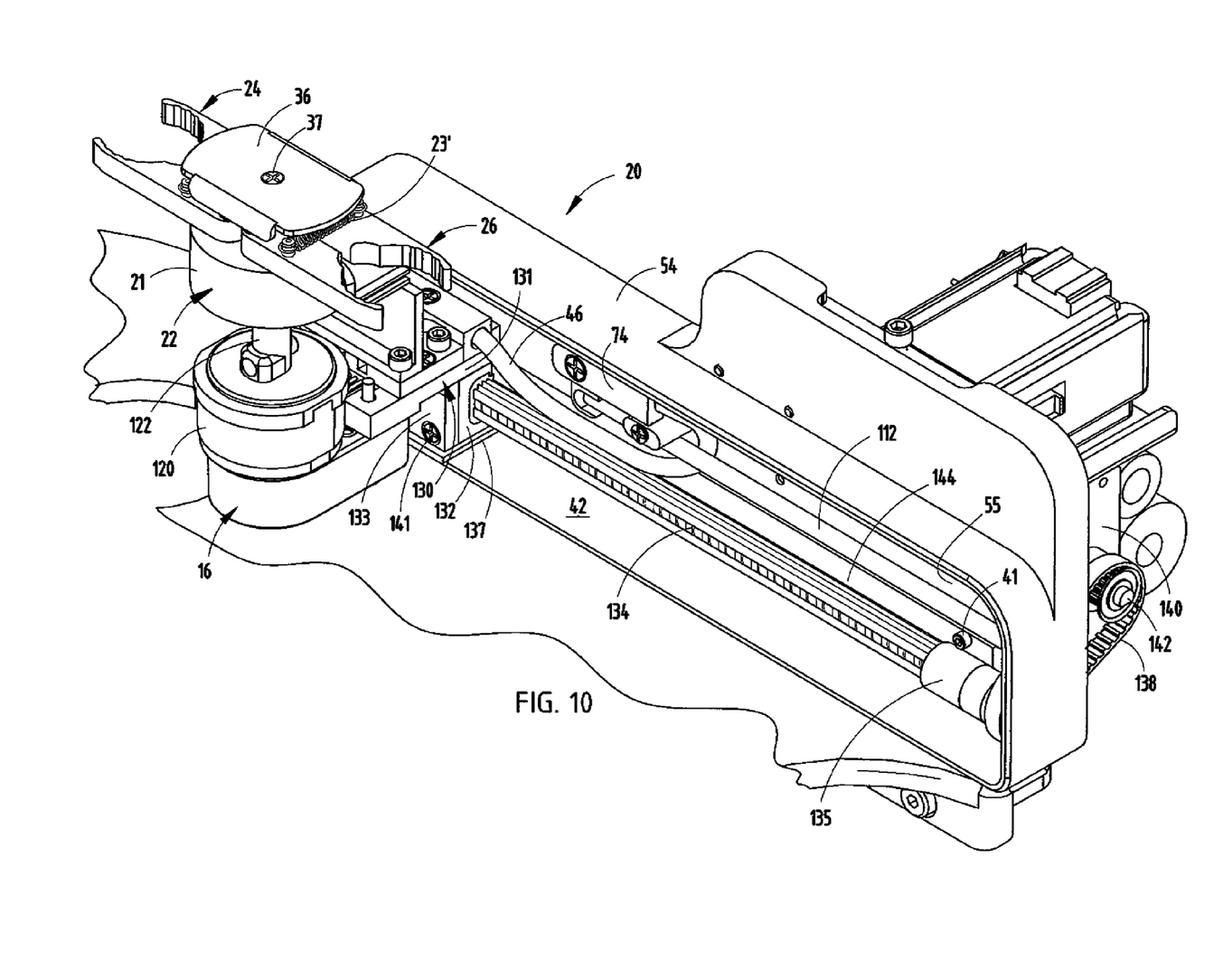
FIG. 10 is an enlarged fragmentary perspective view of the shuttle assembly and housing.

The pairs of gripper arms 24 and 26, each comprising arms 25 and 27, are opened against the force of tension springs 23' holding the arms in a crucible-holding position (shown in FIGS. 3 and 4) by pneumatically actuated, conical actuator pistons 100, as seen in FIG. 7 and best seen in FIGS. 8 and 8A. Springs 23' have ends fitted over posts 29 in arms 25 and 27, as best seen in FIG. 7, to place them in tension. Pistons 100 extend between the pivot arms 25 and 27 at a location between the pivot pins 23 and the spring-holding posts 29. Pistons 100 have a body 102 which is disk shaped and has a peripheral sealing o-ring 109 to movably and sealably mount the pistons within pneumatic cylinders 107 in the rotary head 22. The top 121 (FIGS. 8 and 8A) of rotary head 22 includes a removable cover 105 enclosing pistons 100. Cover 105 has apertures 106 which allow the integral conical tips 103 on the upper side of pistons 100 to extend through head 22, when actuated, to urge pairs of arms 24, 26 to an open crucible releasing position. Tips 103, as seen in FIG. 8A, engage the inner edges 31 of arms 25, 27 acting as a wedge to open the arms to a crucible receiving or releasing position. Pneumatic pressure is selectively applied to each of the piston cylinders 107 and pistons 100 by means of controlled supply lines 108, 110 (FIG. 8). Pistons 100 are returned to a lowered position by compression springs 101 extending between cover 105 (FIGS. 8 and 8A) and the body 102 of the pistons. The pneumatic connection to the pistons 100, as well as the electrical coupling to a rotary actuator 120 (discussed below), is made by a pneumatic and electrical flexible umbilical 46 (FIGS. 9 and 10), which is coupled at one end to shuttle 16 to provide electrical control signals to a rotary actuator 120 and pneumatic pressure individually to pistons 100. Umbilical 46 is allowed to move with the shuttle and is held in an out-of-the-way position from the shuttle drive screw 134 by means of a horizontally extending guide rail 112, as seen in FIGS. 9 and 10. The fixed end of umbilical 46 is coupled to housing 54 by a mounting block 74. The electrical and pneumatic conduits in umbilical 46 are then conventionally coupled to the pneumatic and electrical supplies.

Also mounted to the carriage 130 is a rotary actuator 120 having a vertically extending rotary drive shaft 122 (FIGS. 8-10) coupled to head 22 for reversibly rotating head 22 of shuttle 16 through an arc of 180°. The rotary actuator 120 rotates the rotary head 22 180° in one direction and then reverses direction, such that one pair of gripping arms 26 always handles a new crucible, while the opposite pair of gripping arms 24 handle the contaminated or spent crucibles. The pivoting connections 23 of the pairs of arms 24, 26 are protected by a cover 36 (FIGS. 2-5) by a fastener 37 extending into a vertical post 38, in turn, threaded into a center threaded socket 39 of rotary head 22 (FIG. 8).

Referring now particularly to FIGS. 9-12, the mounting of the shuttle 16 to provide the movement shown in FIGS. 1-5 is described. The shuttle 16 is mounted to a carriage 130 having a polymeric guide block 132 mounted within carriage mounting plate 133 (FIG. 9). The lower surface of carriage mounting plate 133 includes a Teflon® pad 137 which slides along the floor 42 of housing 54. The rotating drive screw 134 is surrounded by an elongated guide 144 secured to back wall 55 of housing 54 by fasteners 41. Guide 144 has an internal bore for receiving drive screw 134 and rotatably supporting the drive screw along its length. The guide 144 also externally slideably receives guide block 132 (as best seen in FIG. 9A), which is secured to plate 133 (FIG. 9) for slideably supporting carriage 130 as it moves between positions shown in FIGS. 2 and 3. The guide block surrounds linear drive screw 134 supported within housing 54 at an end opposite guide block 132 by bearing 135 supported on the back wall 55 of housing 54. The guide block includes a drive nut 134' (FIG. 9A), which drives block 132 and carriage 130 secured thereto by fasteners 141 (FIG. 9) to move the shuttle 16. Elements 132, 134, 135, and 144 can be a commercially available device, such as a rapid drive screw, available from Kerk Motion Products, Inc.

The end of drive screw 134 extends through bearing 135 and is coupled to a gear 136 rotatably driven by a toothed drive belt 138 (best seen in FIG. 9). Belt 138 extends through a slot 139 (FIG. 11) in housing 54 and is coupled to a reversible drive motor 140 through a gear 142 for the reversible rotation of drive screw 134, resulting in the linear movement of carriage 130 between the pedestal 12 and the sample loader 50. The housing 54 for the shuttle assembly 20 includes a front cover plate 56 (FIGS. 1, 3-5, and 7) with a horizontally extending slot 57 to allow an arm 131 (best seen in FIG. 9) coupling shuttle 16 to carriage plate 133 to engage the drive screw 134 throughout the range of movement of the shuttle 16.

Figure 11:
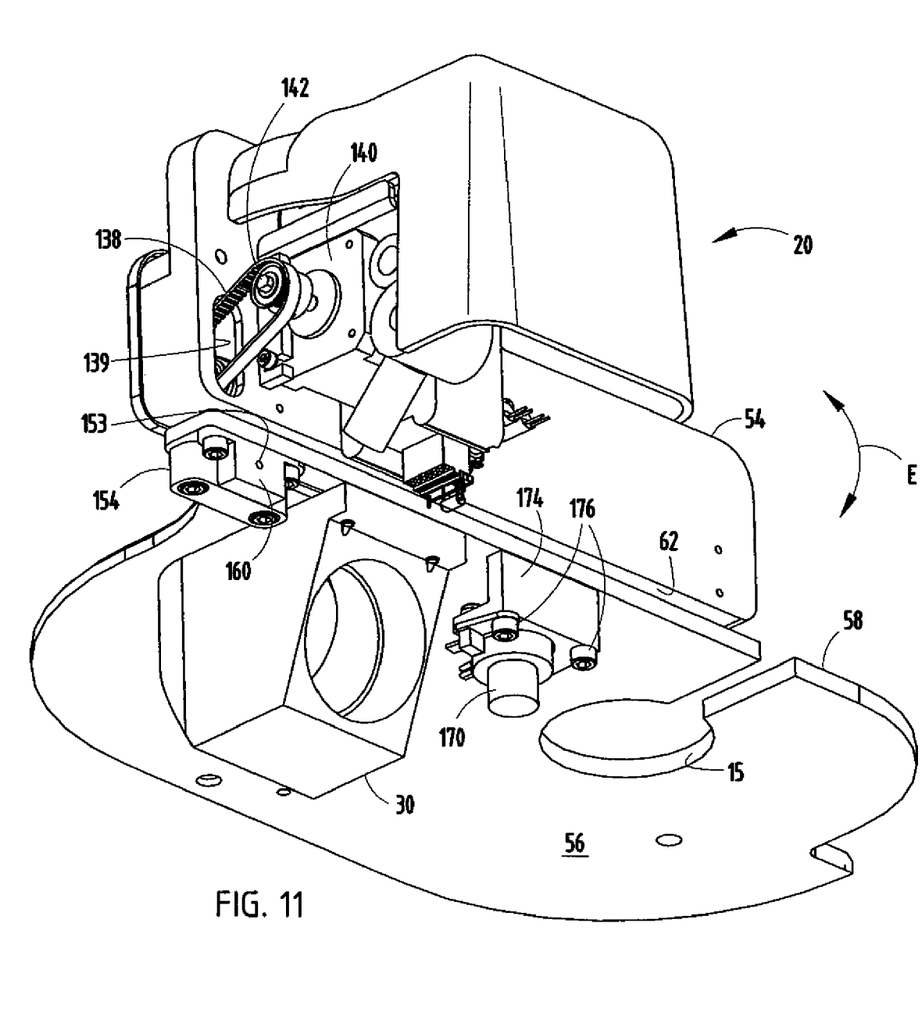
FIG. 11 is a bottom rear perspective view of the shuttle assembly.
Figure 12:
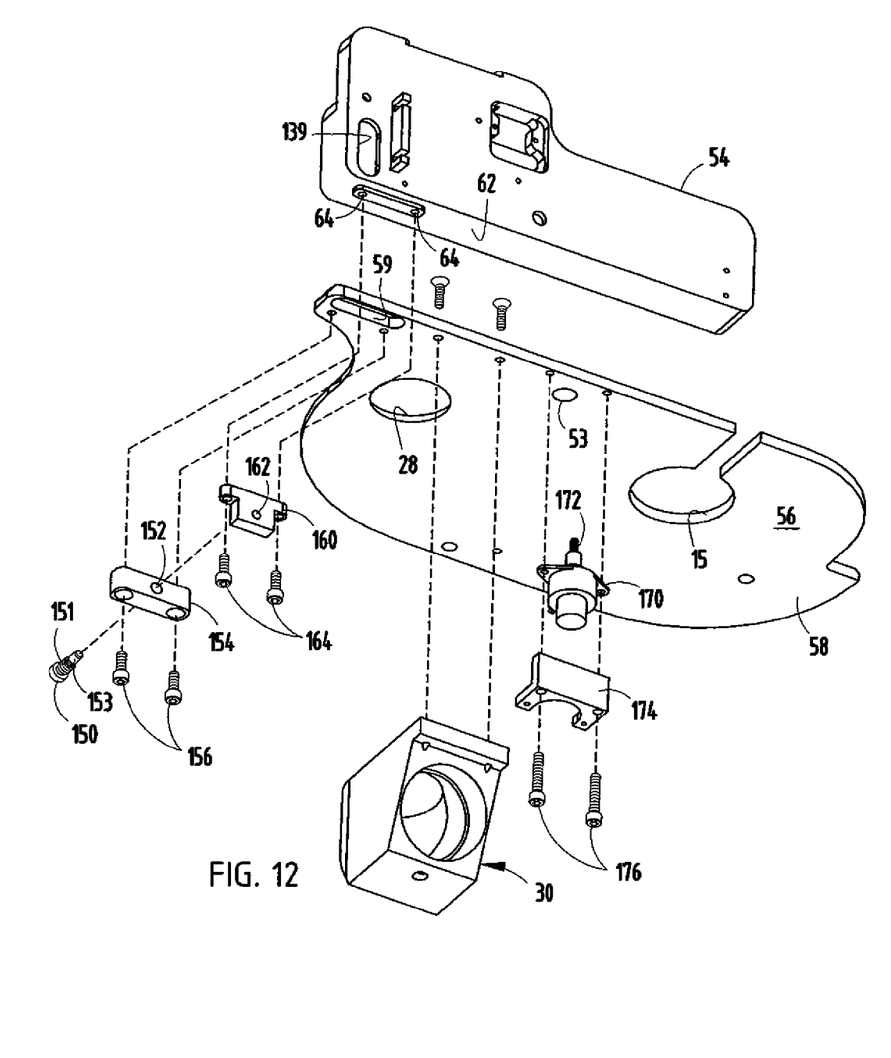
FIG. 12 is an exploded bottom perspective view of a portion of the shuttle assembly showing the pivot mounting of the housing for raising and lowering the gripping arms to lift and place crucibles onto and off of the furnace pedestal.

The shuttle assembly 20, including shuttle 16 with its rotary head 22, gripping arm pairs 24, 26, the shuttle drive mechanism within housing 54, and motor 140, is pivotally mounted to a fixed base plate 58 to be pivotally raised and lowered in a direction indicated by arrow E in FIG. 11 for lifting and placing a crucible from the pairs of arms 24, 26 onto and from the pedestal 12. For such purpose, the mounting housing 54, within which carriage 130 and its drive mechanism are mounted, are pivotally mounted about a pivot axle 150 (FIG. 12). Axle 150 includes a section 151 which extends through an aperture 152 in a mounting block 154. Block 154 is secured by fasteners 156 to the lower surface 56 of plate 58 adjacent an aperture 59 in plate 58. Axle 150 has an end 153 which extends into a threaded aperture 162 in a T-shaped pivot block 160 which is secure to the outer bottom surface 62 of housing 54 by fasteners 164 extending into threaded sockets 64. Block 160 extends through aperture 59 when housing 54 is attached to base plate 58. Aperture 162 in block 160 aligns with aperture 152 in adjacent block 154. When pivot axle 150 is threaded into aperture 162, end 151 of axle 150 provides a pivot correction between housing 54 and its attached components with respect to base plate 58, as seen in FIG. 11.

A linear actuator 170 is mounted in spaced relationship to pivot pin 150 and has a linearly movable shaft 172 which engages the lower surface 62 of housing 54 through opening 53 in base plate 58. Actuator 170 is secured to the underside 56 of plate 58 by a mounting bracket 174 and threaded fasteners 176 (FIG. 12). When actuator 170 is activated, housing 54 pivots upwardly raising the carriage 130 and shutter 16 with gripping arm pairs 24 and 26 upwardly a distance sufficient to lift a crucible off of the pedestal 12. Thus, the rotating head 22 lifts to pick up a spent crucible and rotates and then lowers to deposit a new crucible on pedestal 12. It then moves and opens to discharge the spent crucible into discharge chute 28. The shuttle head 22 then rotates, and the shuttle is moved to the sample loading station 50 where it picks up a new crucible and again moves toward the pedestal 12 where it picks up the spent crucible to repeat the cycle. Plate 58, as seen in FIGS. 3, 4, 11, and 12, includes a slotted aperture 15 for surrounding the furnace pedestal 12 and is secured to the frame 18 (FIG. 1) of furnace 11 in a conventional manner. Mounted to discharge chute 28 (FIGS. 3-5) is an elbow 30 (FIGS. 12 and 13) for directing spent crucibles toward a disposal bin (not shown). Motor 140 is enclosed by a suitable cover 32 (FIGS. 3-5, 10, and 11).

Figure 13:
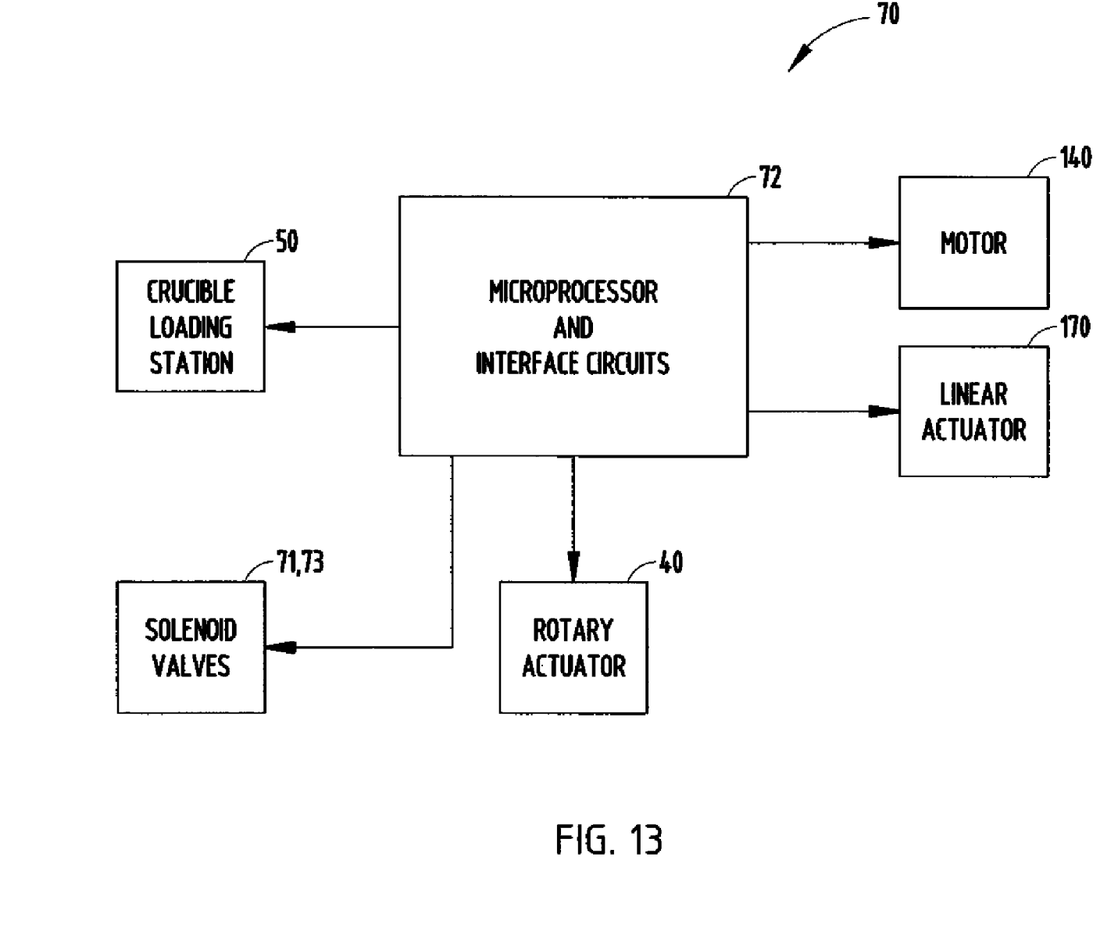
FIG. 13 is an electrical circuit diagram in block form of the control circuit for the system of the present invention.

FIG. 13 is a block electrical diagram of a control circuit 70 for controlling the shuttle assembly 20 in its sequence of operation as described above with reference to FIG. 6. Circuit 70 includes a microprocessor 72 and suitable memory and interface circuits which couple to the drive motor 140 and linear actuator 170 for raising, lowering, and transporting crucibles. Circuit 70 also provides timed signals to rotary actuator 120 to rotate the rotary head 22 of shuttle 16. Microprocessor 72 also actuates the solenoid valves 71 and 73 for actuating the pneumatic supply to control pistons 100 (FIG. 8) for sequentially opening and closing the gripper arm pairs 24 and 26 for alternatively gripping and releasing crucibles therein. The control circuit 70 can be incorporated into the overall control for the instrument 10 and furnace 11 with which the crucible loading and unloading system is mounted including the control of the sample loading station 50.

Thus, with the system of the present invention, sample-holding crucibles can be picked up from a loading station, transported to the induction furnace pedestal whereupon a spent crucible is picked up, the assembly rotated to deposit a new crucible onto the induction furnace pedestal and moved to an intermediate position for discharging the spent crucible and subsequently rotated and moved again to the loading station. By providing opposed gripping arms which are rotated for picking up and discharging crucibles from an induction furnace, the throughput of sample-holding crucibles is greatly improved. This mechanism can also be used for moving crucibles or other articles between first and second positions. As an example, a similar crucible handling assembly can be used to load crucibles onto station 50 from a sample weighing balance.

It will become apparent to those skilled in the art that various modifications to the preferred embodiment of the invention as described herein can be made without departing from the spirit or scope of the invention as defined by the appended claims.

The invention claimed is:

1. A shuttle system for loading and unloading crucibles to and from a furnace associated with an analyzer and a crucible loading station comprising:
   a shuttle including pairs of opposed crucible-gripping arms for simultaneously gripping crucibles on opposite sides of an axis of rotation and further including actuators for selectively opening at least one arm of said pairs of gripping arms to grip and release crucibles;
   a rotating head supporting said pairs of arms;
   a linear drive coupled to said shuttle for moving said rotating head and said gripping arms between a crucible-holding pedestal of a furnace and a loading station for providing sample-holding crucibles for introduction into the furnace; and
   a mechanism for selectively raising and lowering said pairs of gripping arms, wherein said mechanism comprises a fixed base plate, a housing for said shuttle, and a pivot connection between said housing and base.

2. The system as defined in claim 1 and further including a linear actuator coupled between said base and housing for pivoting said housing to raise and lower said pairs of arms.

3. The system as defined in claim 2 wherein said gripping arms are held in a crucible-gripping position by a spring.

4. The system as defined in claim 3 wherein said rotating head is mounted to a carriage and said linear drive comprises a drive screw threadably coupled to said carriage.

5. The system as defined in claim 4 wherein said gripping arms include curved ends for partially circumscribing a cylindrical crucible.

6. A gripping assembly for holding and releasing crucibles comprising:
   a first pair of crucible-gripping arms pivotally mounted on a rotary head;
   a second pair of gripping arms mounted on said head in opposed relationship to said first pair of gripping arms;
   springs for holding said first pair of arms and said second pair of arms in a crucible-holding position;
   a tapered actuator movably coupled between said first and second pairs of arms for selectively opening said gripping arms to release and hold a crucible; and
   wherein said rotary head includes a pair of cylinders for receiving actuating pistons, an actuating piston positioned in each of said cylinders and having a conical tip which extends above said rotary head when actuated, and wherein said pistons are positioned in said head such that said conical tip extends between said pair of arms to open said arms when said pistons are actuated.

7. The gripping assembly as defined in claim 6 wherein said pistons are pneumatically actuated and include a return spring coupled between said pistons and said head for retracting said conical tip from between said pair of arms to allow said arms to close for gripping a crucible.

8. A shuttle assembly for loading and unloading ceramic crucibles between a crucible loading station and a pedestal of an induction furnace associated with an analyzer comprising:
   a shuttle including a pair of opposed crucible-gripping arms for simultaneously gripping two crucibles on opposite sides of an axis of rotation;
   said shuttle including a head for rotatably supporting said arms;
   a linear drive coupled to said shuttle for moving said head and gripping arms between a crucible-holding pedestal of said furnace and a loading station providing sample-holding crucibles for introduction into the furnace, wherein said linear drive also moves said shuttle to a discharge chute for dispensing spent crucibles;
   wherein said shuttle includes a carriage to which said head is mounted and said linear drive includes a drive screw coupled to said carriage for moving said carriage between a furnace and a crucible loading station; and
   a fixed base plate and a housing for said carriage and drive screw, and a pivot connection between said housing and base plate at a location spaced from said shuttle for pivotally raising and lowering said shuttle to lift a crucible from and lower a crucible onto the pedestal.

9. The assembly as defined in claim 8 and further including a linear actuator extending between said base plate and said housing for raising and lowering said shuttle.

10. A crucible loading/unloading shuttle assembly comprising:
    a shuttle including opposed spring-loaded crucible-gripping arms;
    said shuttle including actuators for moving said arms between open and closed positions;
    said shuttle assembly further including a housing and a linear drive positioned in said housing and coupled to said shuttle for moving said shuttle between a furnace and a crucible loading station;
    said shuttle assembly further including a fixed base plate for positioning between a furnace and a crucible loading station wherein said housing is pivotally mounted to said base plate; and
    a second linear actuator coupled between said housing and said base plate for raising and lowering said shuttle.

11. The assembly as defined in claim 10 wherein said shuttle further includes a rotary head to which said gripping arms are coupled.

* * * * *